US011972181B2

(12) United States Patent
Jin et al.

(10) Patent No.: US 11,972,181 B2
(45) Date of Patent: Apr. 30, 2024

(54) BIG DATA-BASED INTELLIGENT ALGORITHM FOR INTRAORAL PROSTHESIS DESIGN SCHEME

(71) Applicant: NANJING PROFETA INTELLIGENT TECHNOLOGY CO., LTD., Nanjing (CN)

(72) Inventors: Yaming Jin, Nanjing (CN); Enlin Pang, Nanjing (CN); Yunhan Du, Nanjing (CN); Hui Gao, Nanjing (CN); Chao Kong, Nanjing (CN); Bao Tang, Nanjing (CN)

(73) Assignee: NANJING PROFETA INTELLIGENT TECHNOLOGY CO., LTD., Nanjing (CN)

( * ) Notice: Subject to any disclaimer, the term of this patent is extended or adjusted under 35 U.S.C. 154(b) by 0 days.

(21) Appl. No.: 18/017,677

(22) PCT Filed: Sep. 11, 2020

(86) PCT No.: PCT/CN2020/114825
§ 371 (c)(1),
(2) Date: Jan. 24, 2023

(87) PCT Pub. No.: WO2022/021551
PCT Pub. Date: Feb. 3, 2022

(65) Prior Publication Data
US 2023/0244830 A1 Aug. 3, 2023

(30) Foreign Application Priority Data

Jul. 29, 2020 (CN) .......................... 202010742778.5

(51) Int. Cl.
*G01N 33/48* (2006.01)
*G01N 33/50* (2006.01)
(Continued)

(52) U.S. Cl.
CPC ............... *G06F 30/20* (2020.01); *G06N 7/02* (2013.01)

(58) Field of Classification Search
CPC .................................. G06F 30/20; G06N 7/02
See application file for complete search history.

(56) References Cited

U.S. PATENT DOCUMENTS 5,044,955 A 9/1991 Jagmin

FOREIGN PATENT DOCUMENTS

| CN | 105184053 A | 12/2015 |
| CN | 108735292 A | 11/2018 |

(Continued)

*Primary Examiner* — Russell S Negin
(74) *Attorney, Agent, or Firm* — Bayramoglu Law Offices LLC (57) ABSTRACT

A big data-based intelligent algorithm for an intraoral prosthesis design scheme establishes an intraoral prosthesis design scheme database based on predetermined data of partially edentulous jaw, and is configured to conduct an accurate search for data of partially edentulous jaw to obtain a recommendation list of an accurate theme and a corresponding design scheme for an intraoral prosthesis design, or conduct a fuzzy search for data of partially edentulous jaw to obtain a recommendation list of a fuzzy theme and a corresponding design scheme for an intraoral prosthesis design. When oriented to a digital design of a removable partial denture, the intelligent system for the intraoral prosthesis design scheme constructed based on this intelligent algorithm displays a large number of intraoral prosthesis design schemes of different design themes to dental technicians in a three-dimensional manner.

7 Claims, 3 Drawing Sheets

(51) Int. Cl.
*G06F 30/20* (2020.01)
*G06N 7/02* (2006.01)

(56) References Cited

FOREIGN PATENT DOCUMENTS

| CN | 108888372 A | 11/2018 |
|---|---|---|
| CN | 109948271 A | 6/2019 |
| CN | 110866712 A | 3/2020 |

BIG DATA-BASED INTELLIGENT ALGORITHM FOR INTRAORAL PROSTHESIS DESIGN SCHEME

CROSS-REFERENCES TO THE RELATED APPLICATIONS

The application is a national stage entry of PCT/CN2020/114825 filed on Sep. 11, 2020, which claims priority to Chinese patent applications No. 202010742778.5 filed on Jul. 29, 2020, the entire contents of which are incorporated herein by reference.

TECHNICAL FIELD

The present disclosure relates to the technical field of computer-aided algorithms, and specifically, to a big data-based intelligent algorithm for an intraoral prosthesis design scheme.

BACKGROUND

Although existing intraoral prosthesis design schemes meet the requirements of digital design, expert experience needs to be accumulated for a long period of time, and junior dental technicians need to memorize a large number of cases in order to design a qualified product. To design an intraoral prosthesis, although factors such as intraoral anatomy, force analysis, and safety and hygiene of patients need to be comprehensively considered, there are a plurality of design concepts at a specific design and implementation stage of the intraoral prosthesis, and dental technicians/doctors usually only specialize in one design concept. For example, the top domestic Peking University School of Stomatology and West China School of Stomatology have a big difference in the design concept of removable partial dentures. At the same time, with the gradual improvement of domestic living conditions, patients have put forward higher requirements for the design of the intraoral prosthesis. Therefore, there is an urgent need in the market for an intelligent recommendation algorithm and system that broaden the design concept of dental technicians/doctors of the intraoral prosthesis.

SUMMARY

An objective of the present disclosure is to provide a big data-based intelligent algorithm for an intraoral prosthesis design scheme in order to overcome the deficiencies of the prior art. The intelligent algorithm first establishes an intraoral prosthesis design scheme database based on predetermined data of partially edentulous jaw, and is configured to conduct an accurate search for data of partially edentulous jaw to obtain a recommendation list of an accurate theme and a corresponding design scheme for an intraoral prosthesis design, or conduct a fuzzy search for data of partially edentulous jaw to obtain a recommendation list of a fuzzy theme and a corresponding design scheme for an intraoral prosthesis design. When oriented to a digital design of a removable partial denture, the intelligent system for the intraoral prosthesis design scheme constructed based on this intelligent algorithm displays a large number of intraoral prosthesis design schemes of different design themes to dental technicians in a three-dimensional manner.

To resolve the foregoing technical problem, the present disclosure provides the following technical solutions.

The big data-based intelligent algorithm for the intraoral prosthesis design scheme provided in the present disclosure includes the following steps:

Step S1: establishing an intraoral prosthesis design scheme database based on predetermined data of partially edentulous jaw,
  where the database provides two data search paths, namely an accurate search for data of partially edentulous jaw and a fuzzy search for data of partially edentulous jaw.

Step S2: acquiring data of partially edentulous jaw of a current dentition by using a scanning device, and performing accurate encoding on the data of partially edentulous jaw of the current dentition to obtain one group of dentition information accurate code,
  where the dentition information accurate code includes: accurate code of partially edentulous jaw information, dentition accurate location code, and other dentition information code.

The accurate code of partially edentulous jaw information is encoded data obtained by numbering all teeth in the current dentition according to an accurate encoding rule after an initial posture of the dentition is adjusted, where a default format of the accurate code of partially edentulous jaw information includes 1 letter and 16 digits, and the accurate encoding rule is as follows:
  (1) the letter: if the dentition represented by the encoded data belongs to an upper jaw, the letter is U, or if the dentition represented by the encoded data belongs to a lower jaw, the letter is L; and
  (2) the digits: after the initial posture of the dentition is adjusted, teeth information in the dentition is sequentially encoded clockwise from left to right, and if a tooth is present at a location, code of the tooth is 1, or if a tooth is absent at the location, code of the tooth is 0.

The fuzzy code of partially edentulous jaw information is obtained by performing data block division on the accurate code of partially edentulous jaw information, where a format of the fuzzy code of partially edentulous jaw information includes 1 letter, several "0" data blocks, several "1" digits, and several "1" data blocks, where a data block division rule is specifically as follows:
  (1) division of the "0" data blocks: all adjacent and successive "0"s are divided into one "0" data block based on one piece of accurate code of partially edentulous jaw information, and the data block is marked as i–0, where i represents a number of data "0"s in the data block, namely a length of the "0" data block;
  (2) division of the "1" digits: each alternative abutment tooth is used as a separate "1" digit based on the one piece of accurate code of partially edentulous jaw information; and
  (3) division of the "1" data blocks: after each of the alternative abutment teeth is excluded, all adjacent and successive "1"s are divided into one "1" data block based on the one piece of accurate code of partially edentulous jaw information, and the data block is marked as j–1, where j represents a number of data "1"s in the data block, namely a length of the "I" data block.

The dentition accurate location code is obtained by encoding a dentition accurate location based on the accurate code of partially edentulous jaw information after the initial posture of the dentition is adjusted, and a specific rule is as follows: accurate location code is sequentially 1, 2, 3, 4, 5, 6, 7, 8, 9, 10, 11, 12, 13, 14, 15, and 16 in a clockwise direction from left to right.

The dentition fuzzy location code is obtained by calculating a data block center location of the fuzzy code of partially edentulous jaw information, and a calculation rule of the data block center location is: the center location is calculated for each of the "0" data blocks or each of the "1" data blocks in the fuzzy code of partially edentulous jaw information, to be specific, an average value is calculated for the accurate location code inside the dentition region corresponding to each of the "0" data blocks or each of the "1" data blocks.

The other dentition information code is other teeth information obtained based on the one piece of accurate code of partially edentulous jaw information, specifically as follows:
(1) a tooth loosening degree coefficient: for a tooth with code of 1, if code of a tooth/teeth on either side or both sides of the tooth is 0, the tooth is defined as an alternative abutment tooth, and a loosening degree coefficient of the tooth is obtained with priority; for a tooth with code of 1, if code of teeth on both sides of the tooth is 1, the tooth is defined as a general abutment tooth, and a loosening degree coefficient of the tooth is obtained when necessary; and the loosening degree coefficient is any decimal between 0 and 1, and a smaller number represents a more severe tooth loosening degree; and
(2) a tooth rotation matrix: for a tooth with code of 1, a three-dimensional rotation matrix $M_t$ is defined to reflect a relationship between an actual space state and a standard healthy state of the tooth, where the subscript t is the dentition accurate location code.

Step S3: including a plurality of groups of intraoral prosthesis component information in the intraoral prosthesis design scheme database, where the intraoral prosthesis component information includes: an intraoral prosthesis component type sequence and intraoral prosthesis component location code;
where the intraoral prosthesis component type sequence is a sequence formed for an intraoral prosthesis component type according to the dentition accurate location code in the step S2.

Further, the intraoral prosthesis component type includes: a first intraoral prosthesis component type, a second intraoral prosthesis component type, and a third intraoral prosthesis component type. The first intraoral prosthesis component type is an important component strongly related to the dentition accurate location code; the second intraoral prosthesis component type is a secondary component weakly related to the dentition accurate location code; and the third intraoral prosthesis component type is a component that connects the first intraoral prosthesis component type to the second intraoral prosthesis component type.

The intraoral prosthesis component location code includes: intraoral prosthesis component accurate location code and intraoral prosthesis component fuzzy location code. The intraoral prosthesis component accurate location code is consistent with the dentition accurate location code, and the intraoral prosthesis component fuzzy location code is consistent with the dentition fuzzy location code.

Step S4: obtaining intraoral prosthesis design theme code according to the accurate code of partially edentulous jaw information in the step S2 and the intraoral prosthesis component information in the step S3, where the intraoral prosthesis design theme code includes: intraoral prosthesis design accurate theme code and intraoral prosthesis design fuzzy theme code.

The intraoral prosthesis design accurate theme code is a combination of a plurality of groups of accurately matched intraoral prosthesis component information, and the accurately matched intraoral prosthesis component information means complete consistency in both the intraoral prosthesis component type sequence and the intraoral prosthesis component location code.

The intraoral prosthesis design fuzzy theme code is a combination of a plurality of groups of fuzzily matched intraoral prosthesis component information, and the fuzzily matched intraoral prosthesis component information means complete consistency in the intraoral prosthesis component type sequence but inconsistency in the intraoral prosthesis component location code.

Step S5: providing, by this algorithm, two different recommendation lists of intraoral prosthesis design schemes according to different intraoral prosthesis design concepts, specifically as follows:
step S5-1: in all intraoral prosthesis design accurate theme code obtained in the step S4, obtaining m pieces of intraoral prosthesis design accurate theme code based on one piece of accurate code of partially edentulous jaw information, and therefore finally obtaining a first recommendation list including the m pieces of intraoral prosthesis design accurate theme code; and
step S5-2: calculating to obtain n pieces of accurate code of partially edentulous jaw information with smallest distance function values in all intraoral prosthesis design fuzzy theme code obtained in the step S4, where m pieces of intraoral prosthesis design accurate theme code are obtained based on one piece of accurate code of partially edentulous jaw information, one piece of intraoral prosthesis design accurate theme code corresponds to one piece of intraoral prosthesis design fuzzy theme code, and therefore finally obtaining a second recommendation list including k pieces of intraoral prosthesis design fuzzy theme code; where k≤n×m.

A sorting method of the intraoral prosthesis design fuzzy theme code in the second recommendation list is as follows:
(1) Sorting based on partially edentulous jaw information of a patient;
performing sorting according to an ascending order of distance function values of the accurate code of partially edentulous jaw information; to be specific, a smaller distance function value indicates a higher sorting location of the intraoral prosthesis design fuzzy theme code corresponding to the accurate code of partially edentulous jaw information.

For any two pieces of different accurate code of partially edentulous jaw information, a case in which the two pieces of different accurate code of partially edentulous jaw information correspond to identical fuzzy code of partially edentulous jaw information exists; in this case, a calculation method of a distance function between the two pieces of different accurate code of partially edentulous jaw information is as follows:

$$D=\Sigma_1^i |(a_i-b_i)|$$

where the dentition fuzzy location code of first accurate code of partially edentulous jaw information is $a_1 a_2 \ldots a_i$, and the dentition fuzzy location code of second accurate code of partially edentulous jaw information is $b_1 b_2 \ldots b_i$, and $1 \le i \le 16$.

Optionally, sorting is performed according to the other dentition information code, for example, multidimensional information such as the tooth loosening degree coefficient and the tooth rotation matrix.
(2) Custom sorting based on subjective and objective scoring results;

experts subjectively score design themes in a plurality of dimensions such as hygiene, mechanical balance, and aesthetics, at the same time, testing means such as finite element calculation and in vitro mechanical verification are introduced to objectively score the design themes, and these subjective and objective scoring results provide a basis for user-defined theme sorting.

A process of supplementing the intraoral prosthesis design scheme database with new partially edentulous jaw information code is specifically as follows: when no design theme corresponding to new data of partially edentulous jaw is found in the database by either the accurate search or the fuzzy search for the data of partially edentulous jaw, a dental technician or a doctor first complete a concept of a required intraoral prosthesis design scheme and submit the intraoral prosthesis design scheme, and various new accurate code and fuzzy code of the data of partially edentulous jaw are automatically created.

The big data-based intelligent algorithm for the intraoral prosthesis design scheme provided in the present disclosure has the following benefits compared with the prior art.

(1) The intraoral prosthesis design scheme database established based on the predetermined data of partially edentulous jaw not only stores a large quantity of design theme cases, but also includes multi-source subjective and objective evaluation information, including subjective scores given by experts for design themes in a plurality of dimensions such as hygiene, mechanical balance, and aesthetics, objective simulation evaluation performed by using finite element calculation, objective scores for design themes given by using testing means such as in vitro mechanical verification, and the like.

(2) The provided intelligent system is directly used in fields such as a digital design of a removable partial denture, to recommend intraoral prosthesis design schemes of a plurality of design concepts, and display the intraoral prosthesis design schemes in a three-dimensional form, so that without memorizing a large number of cases, dental technicians could master a plurality of design concepts in a short time under the assistance of the system, and select a suitable intraoral prosthesis design scheme for a patient under the assistance of the algorithm, thereby finally improving satisfaction of patients.

DETAILED DESCRIPTION OF THE EMBODIMENTS

The present disclosure will be further described hereafter in detail with reference to embodiments.

Embodiment 1. The present disclosure provides a big data-based intelligent algorithm for an intraoral prosthesis design scheme, and the intelligent algorithm includes the following steps.

Step S1: an intraoral prosthesis design scheme database is established based on predetermined data of partially edentulous jaw, where the database provides two data search paths, namely an accurate search for data of partially edentulous jaw and a fuzzy search for data of partially edentulous jaw.

Further, the database includes data of partially edentulous jaw, intraoral prosthesis component data, and intraoral prosthesis design theme data. Before the database is constructed, accurate encoding and fuzzy encoding are first performed on the data of partially edentulous jaw, the intraoral prosthesis component data, and the intraoral prosthesis design theme data.

Furthermore, accurate code and fuzzy code in the database satisfy the following relationship: one group of accurate code corresponds to one group of fuzzy code, and one group of fuzzy code corresponds to a plurality of groups of accurate code.

Step S2: data of partially edentulous jaw of a current dentition is acquired by using a scanning device, and accurate encoding is performed on the data of partially edentulous jaw of the current dentition to obtain one group of dentition information accurate code.

Figure 1:
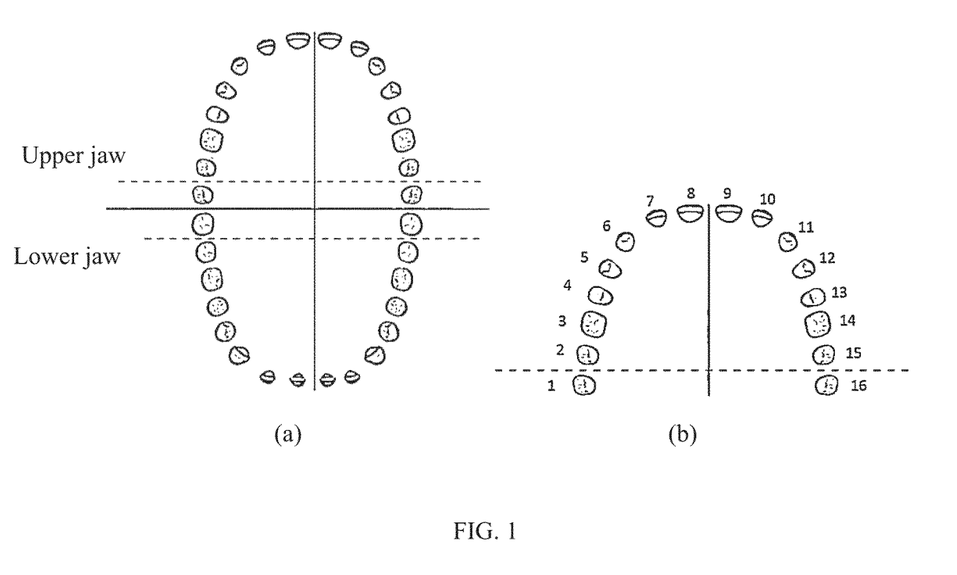
FIG. 1 is a schematic diagram of an upper-jaw and lower-jaw model to which a big data-based intelligent algorithm for an intraoral prosthesis design scheme provided in the present disclosure is applied. A process from FIG. 1(a) to FIG. 1(b) is adjustment of a dentition initial posture.

Before accurate encoding is performed, an initial posture of the dentition first needs to be adjusted. It is seen from the upper-jaw and lower-jaw model shown in FIG. 1(a) that, neither of the numbers of teeth in the upper jaw and the lower jaw exceeds 16, and teeth located in the upper jaw bone and the lower jaw bone are successively arranged in their respective alveolar bones to form arches each in the shape of a parabola. Either in the upper-jaw model or the lower-jaw model, a three-dimensional direction of a digital model is first adjusted, so that tooth roots face inward perpendicular to a screen, and the parabola of a dental arch is kept downward, as shown in FIG. 1(b). A process from FIG. 1(a) to FIG. 1(b) is adjustment of the dentition initial posture.

The dentition information accurate code includes: accurate code of partially edentulous jaw information, dentition accurate location code, and other dentition information code.

The accurate code of partially edentulous jaw information is encoded data obtained by numbering all teeth in the dentition according to an accurate encoding rule after the initial posture of the dentition is adjusted, where a default format of the encoded data includes 1 letter and 16 digits, and the accurate encoding rule is as follows:

(1) the letter: if the dentition represented by the encoded data belongs to an upper jaw, the letter is U, or if the dentition represented by the encoded data belongs to a lower jaw, the letter is L; and (2) the digits: after the initial posture of the dentition is adjusted, teeth information in the dentition is sequentially encoded clockwise from left to right, and if a tooth is present at a location, code of the tooth is 1, or if a tooth is absent at the location, code of the tooth is 0.

In this preferred embodiment, the accurate code of partially edentulous jaw information is U0100100100011111.

When inputting a jaw model, there are many ways to obtain the accurate code of partially edentulous jaw information, including user's manual input and a combination of automatic generation by means of an algorithm such as a machine learning algorithm or a graphics algorithm with user's confirmation.

Furthermore, the dentition accurate location code is inferred based on one piece of accurate code of partially edentulous jaw information. A dentition accurate location is encoded after the initial posture of the dentition is adjusted, and an encoding rule is specifically as follows: the accurate location code is sequentially 1, 2, 3, 4, 5, 6, 7, 8, 9, 10, 11, 12, 13, 14, 15, and 16 in a clockwise direction from left to right.

Furthermore, the other teeth information is obtained based on the one piece of accurate code of partially edentulous jaw information, specifically as follows:

(1) a tooth loosening degree coefficient: for a tooth with code of 1, if code of a tooth/teeth on either side or both sides of the tooth is 0, the tooth is defined as an alternative abutment tooth, and a loosening degree coefficient of the tooth is obtained with priority; for a tooth with code of 1, if code of teeth on both sides of the tooth is 1, the tooth is defined as a general abutment tooth, and a loosening degree coefficient of the tooth is obtained when necessary; and the loosening degree coefficient is any decimal between 0 and 1, and a smaller number represents a more severe tooth loosening degree; and (2) a tooth rotation matrix: for a tooth with code of 1, a three-dimensional rotation matrix $M_t$ is defined to reflect a relationship between an actual space state and a standard healthy state of the tooth, where the subscript t is the dentition accurate location code.

In conventional medicine, a tip angle and a torque angle of a tooth are used to define a deformity degree of the tooth, but such a manner is not suitable for large-scale computations performed by a computer. In the present disclosure, the tip angle and rotation angle are respectively converted into angle-axis representation matrices, namely M(tip) and M(rotation). In this case, a distortion relationship matrix is represented as $M_t = M(tip) \times M(rotation)$.

In an angle-axis representation method, in three dimensions, rotation is defined by using a single rotation angle $\theta$ and a unit vector direction $\hat{v}=(x,y,z)$ that the rotation angle $\theta$ surrounds:

$$M(\hat{v}, \theta) = \begin{bmatrix} \cos\theta + (1-\cos)x^2 & (1-\cos\theta)xy - (\sin\theta)z & (1-\cos\theta)xz + (\sin\theta)y \\ (1-\cos\theta)yx + (\sin\theta)z & \cos\theta + (1-\cos\theta)y^2 & (1-\cos\theta)yz - (\sin\theta)x \\ (1-\cos\theta)zx - (\sin\theta)y & (1-\cos\theta)zy + (\sin\theta)x & \cos\theta + (1-\cos\theta)z^2 \end{bmatrix}$$

In this preferred embodiment, the other teeth information corresponding to the accurate code of partially edentulous jaw information U0100100100011111 is shown in the table below:

| Upper jaw/Lower jaw | Location code | | | | | | | | | | | | | | | |
|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 |
| Tooth code U | 0 | 1 | 0 | 0 | 1 | 0 | 0 | 1 | 0 | 0 | 0 | 1 | 1 | 1 | 1 | 1 |
| Loosening degree coefficient | | 0.7 | | | 0.8 | | | 0.9 | | | | 0.5 | 1 | 1 | 1 | 1 |
| Rotation matrix | | $M_2$ | | | $M_5$ | | | $M_8$ | | | | $M_{12}$ | $M_{13}$ | $M_{14}$ | $M_{15}$ | $M_{16}$ |

In the table above, teeth with location code of 2, 5, 8, and 12 are alternative abutment teeth, and teeth with location code of 13, 14, 15, and 16 are general abutment teeth. When a loosening degree coefficient of the alternative abutment tooth with location code of 12 is excessively small, preferably less than 0.5, a loosening degree coefficient of a tooth adjacent to the alternative abutment tooth and with tooth code of 1, namely, the general abutment tooth with location code of 13, needs to be obtained, and the general abutment tooth is used as an optional alternative abutment tooth.

Data block division is performed on the accurate code of partially edentulous jaw information, to obtain the fuzzy code of partially edentulous jaw information. The data block division means dividing all adjacent and successive identical code into one data block based on one piece of accurate code of partially edentulous jaw information. Specifically, all adjacent and successive "0"s are divided into one "0" data block, and after each alternative abutment tooth is excluded, all adjacent and successive "1"s are divided into one "1" data block.

A format of the fuzzy code of partially edentulous jaw information includes 1 letter, several "0" data blocks, several "1" digits, and several "1" data blocks. A fuzzy encoding rule is specifically as follows:

(1) division of the "0" data blocks: all adjacent and successive "0"s are divided into one data block based on the one piece of accurate code of partially edentulous jaw information, and the data block is marked as i–0, where i represents a number of data "0"s in the data block, namely a length of the "0" data block;

(2) division of the "1" digits: each alternative abutment tooth is used as a separate "1" digit based on the one piece of accurate code of partially edentulous jaw information; and (3) division of the "1" data blocks: after each of the alternative abutment teeth is excluded, all adjacent and successive "1"s are divided into one data block based on the one piece of accurate code of partially edentulous jaw information, and the data block is marked as j–1, where j represents a number of data "1"s in the data block, namely a length of the "1" data block.

In this preferred embodiment, fuzzy code corresponding to the accurate code of partially edentulous jaw information U0100100100011111 is U[1-0]1 [2-0]1[2-0]1[3-0]1[3-1]1. Further, lengths of the "0" data blocks and "1" data blocks are omitted to obtain simplified fuzzy code. Then the fuzzy code is simplified into U0101010111. An operational speed of the algorithm is prominently improved through fuzzy code and simplified fuzzy code.

prosthesis component type is a secondary component weakly related to the dentition accurate location code, for example, a component such as a minor connector and a retentive pin; and the third intraoral prosthesis component type is a component that connects the first intraoral prosthesis component type to the second intraoral prosthesis component type, for example, a component such as a major connector and a lingual bar.

Figure 2:
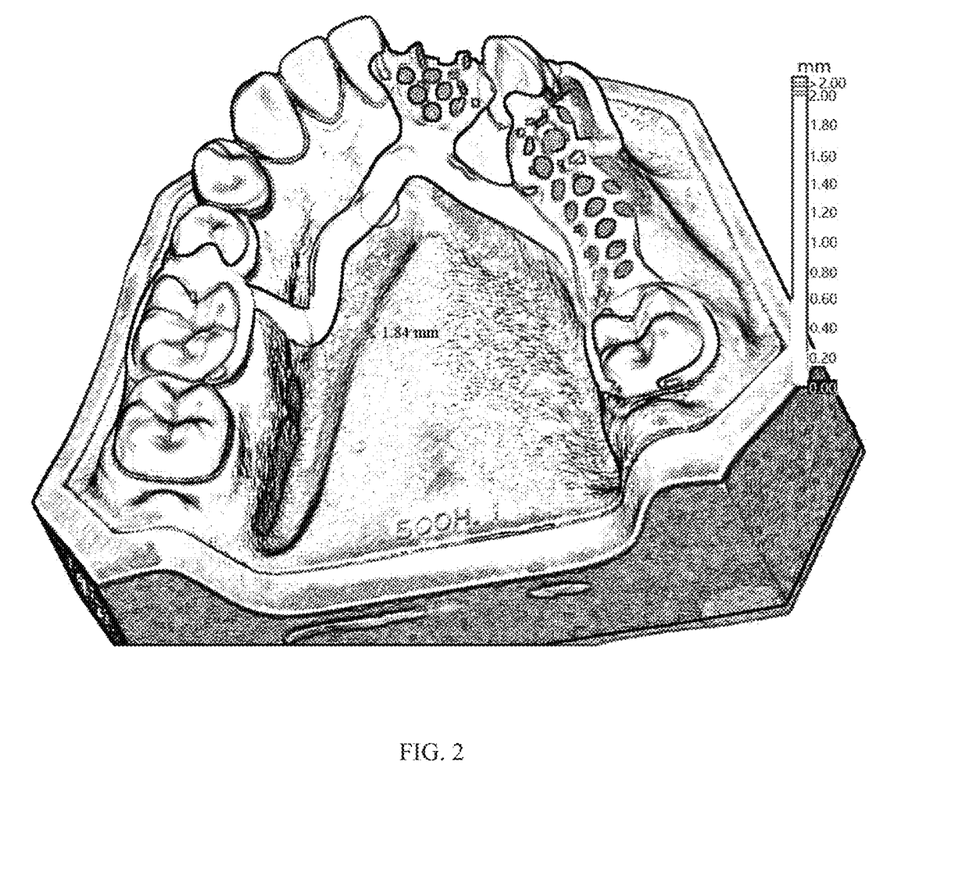
FIG. 2 is a three-dimensional model diagram of a removable partial denture to which a big data-based intelligent algorithm for an intraoral prosthesis design scheme provided in the present disclosure is applied.

In this preferred embodiment, using a removable partial denture shown in FIG. 2 as an example, information about a possible intraoral prosthesis component type is shown in the table below:

| Upper jaw/Lower jaw | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| | | | | | | | Location code | | | | | | | | | |
| Tooth code | U | 0 | 1 | 0 | 0 | 1 | 0 | 0 | 1 | 0 | 0 | 0 | 1 | 1 | 1 | 1 | 1 |
| Component information | | | | Combined clasp | | | | | Retentive mesh | | T-shaped clasp | Retentive mesh | | | Three-arm clasp | |
| | | | | Minor connector | | | | | Spiral retentive pin | Spiral retentive pin | | | | | | |
| | | | | | | | | | | Lingual bar | | | | | | |

Furthermore, dentition fuzzy location code is inferred based on one piece of fuzzy code of partially edentulous jaw information. After the initial posture of the dentition is adjusted, transcoding is implemented on the dentition accurate location in a manner of dentition region division. The encoding rule is: separately calculating a center location of each of the "0" data blocks and a center location of each of the "1" data blocks, to be specific, an average value is calculated for accurate location code inside a dentition region corresponding to each of the "0" data blocks or each of the "1" data blocks.

In this preferred embodiment, in a clockwise direction from left to right, the dentition fuzzy location code is sequentially 1, 2, (3+4)/2, 5, (6+7)/2, 8, (9+11)/2, 12, (13+15)/2, and 16.

The analysis above shows that, one piece of accurate code of partially edentulous jaw information corresponds to one piece of fuzzy code of partially edentulous jaw information, and one piece of fuzzy code of partially edentulous jaw information corresponds to a plurality of pieces of accurate code of partially edentulous jaw information.

Step S3: a plurality of groups of intraoral prosthesis component information are included in the intraoral prosthesis design scheme database, where the intraoral prosthesis component information includes: an intraoral prosthesis component type sequence and intraoral prosthesis component location code.

The intraoral prosthesis component type sequence is a sequence formed for the intraoral prosthesis component type based on the dentition accurate location code, namely digits 1 to 16. The intraoral prosthesis component type includes: a first intraoral prosthesis component type, a second intraoral prosthesis component type, and a third intraoral prosthesis component type.

Further, the first intraoral prosthesis component type is an important component strongly related to the dentition accurate location code, for example, a component such as a clasp, a retentive mesh and an occlusal rest, the second intraoral Therefore, the intraoral prosthesis component type sequence is: [combined clasp (3-4), retentive mesh (9-10), T-shaped clasp (11), retentive mesh (12-14), three-arm clasp (15), minor connector (3), spiral retentive pin (9), spiral retentive pin (10), and lingual bar (4-13)].

The intraoral prosthesis component location code includes: intraoral prosthesis component accurate location code and intraoral prosthesis component fuzzy location code. The intraoral prosthesis component accurate location code is consistent with the dentition accurate location code, and the intraoral prosthesis component fuzzy location code is consistent with the dentition fuzzy location code.

Step S4: intraoral prosthesis design theme code is obtained according to the accurate code of partially edentulous jaw information in the step S2 and the intraoral prosthesis component information in the step S3, where the intraoral prosthesis design theme code includes: intraoral prosthesis design accurate theme code and intraoral prosthesis design fuzzy theme code.

Further, targeted fine tuning is also performed to the encoding rule, based on the intraoral prosthesis component type, for the intraoral prosthesis design theme code obtained in this step. A fine tuning rule is generally combining a plurality of subcategories into one category according to experience.

The intraoral prosthesis design accurate theme code is a combination of a plurality of groups of accurately matched intraoral prosthesis component information, and the accurately matched intraoral prosthesis component information means complete consistency in both the intraoral prosthesis component type sequence and the intraoral prosthesis component location code.

In this preferred embodiment, using a removable partial denture as an example, possible intraoral prosthesis design accurate theme code is as follows:

Accurate theme code=[combined clasp (3-4), retentive mesh (9-10), T-shaped clasp (11), retentive mesh (12-14), three-arm clasp (15), minor connector (3), spiral retentive pin (9), spiral retentive pin (10), and lingual bar (4-13)].

The intraoral prosthesis design fuzzy theme code is a combination of a plurality of groups of fuzzily matched intraoral prosthesis component information, and the fuzzily matched intraoral prosthesis component information means complete consistency in the intraoral prosthesis component type sequence but inconsistency in the intraoral prosthesis component location code.

In this preferred embodiment, using a removable partial denture as an example, possible intraoral prosthesis design fuzzy theme code is as follows:

Fuzzy theme code=[combined clasp, retentive mesh, T-shaped clasp, retentive mesh, three-arm clasp, minor connector, spiral retentive pin, spiral retentive pin, and lingual bar].

It can be seen that, each piece of intraoral prosthesis design accurate theme code corresponds to one piece of intraoral prosthesis design fuzzy theme code, and one piece of intraoral prosthesis design fuzzy theme code corresponds to a plurality of pieces of intraoral prosthesis design accurate theme code.

Step S5: This algorithm provides two different recommendation lists of intraoral prosthesis design schemes according to different intraoral prosthesis design concepts, specifically as follows:

step S5-1: in all intraoral prosthesis design accurate theme code obtained in the step S4, m pieces of intraoral prosthesis design accurate theme code are obtained based on one piece of accurate code of partially edentulous jaw information, and therefore a first recommendation list including the m pieces of intraoral prosthesis design accurate theme code is finally obtained; and step S5-2: n pieces of accurate code of partially edentulous jaw information with smallest distance function values are obtained through calculation in all intraoral prosthesis design fuzzy theme code obtained in the step S4, where m pieces of intraoral prosthesis design accurate theme code are obtained based on one piece of accurate code of partially edentulous jaw information, one piece of intraoral prosthesis design accurate theme code corresponds to one piece of intraoral prosthesis design fuzzy theme code, and therefore a second recommendation list including k pieces of intraoral prosthesis design fuzzy theme code is finally obtained; where k≤n×m.

In actual application, the first recommendation list and the second recommendation list are respectively provided by the accurate search for data of partially edentulous jaw and the fuzzy search for data of partially edentulous jaw.

In the first recommendation list and the second recommendation list, a sorting method of the intraoral prosthesis design theme code includes two manners:

(1) Sorting based on partially edentulous jaw information of a patient;

sorting is performed according to an ascending order of distance function values of the accurate code of partially edentulous jaw information; to be specific, a smaller distance function value indicates a higher sorting location of the intraoral prosthesis design fuzzy theme code corresponding to the accurate code of partially edentulous jaw information.

For any two pieces of different accurate code of partially edentulous jaw information, a case in which the two pieces of different accurate code of partially edentulous jaw information correspond to identical fuzzy code of partially edentulous jaw information exists; in this case, a calculation method of a distance function between the two pieces of different accurate code of partially edentulous jaw information is as follows:

$$D=\Sigma_1{}^i|(a_i-b_i)|$$

where the dentition fuzzy location code of first accurate code of partially edentulous jaw information is $a_1$ $a_2 \ldots a_i$, and the dentition fuzzy location code of second accurate code of partially edentulous jaw information is $b_1$ $b_2 \ldots b_i$, and $1 \leq i \leq 16$.

Optionally, sorting is performed according to the other dentition information code, for example, multidimensional information such as the tooth loosening degree coefficient and the tooth rotation matrix.

(2) Custom sorting based on subjective and objective scoring results;

experts subjectively score design themes in a plurality of dimensions such as hygiene, mechanical balance, and aesthetics, at the same time, testing means such as finite element calculation and in vitro mechanical verification are introduced to objectively score the design themes, and these subjective and objective scoring results provide a basis for user-defined theme sorting.

A process of supplementing the intraoral prosthesis design scheme database with new partially edentulous jaw information code is specifically as follows: when no design theme corresponding to new data of partially edentulous jaw is found in the database by either the accurate search or the fuzzy search for the data of partially edentulous jaw, a dental technician or a doctor first complete a concept of a required intraoral prosthesis design scheme and submit the intraoral prosthesis design scheme, and various new accurate code and fuzzy code of the data of partially edentulous jaw are automatically created.

Figure 3:
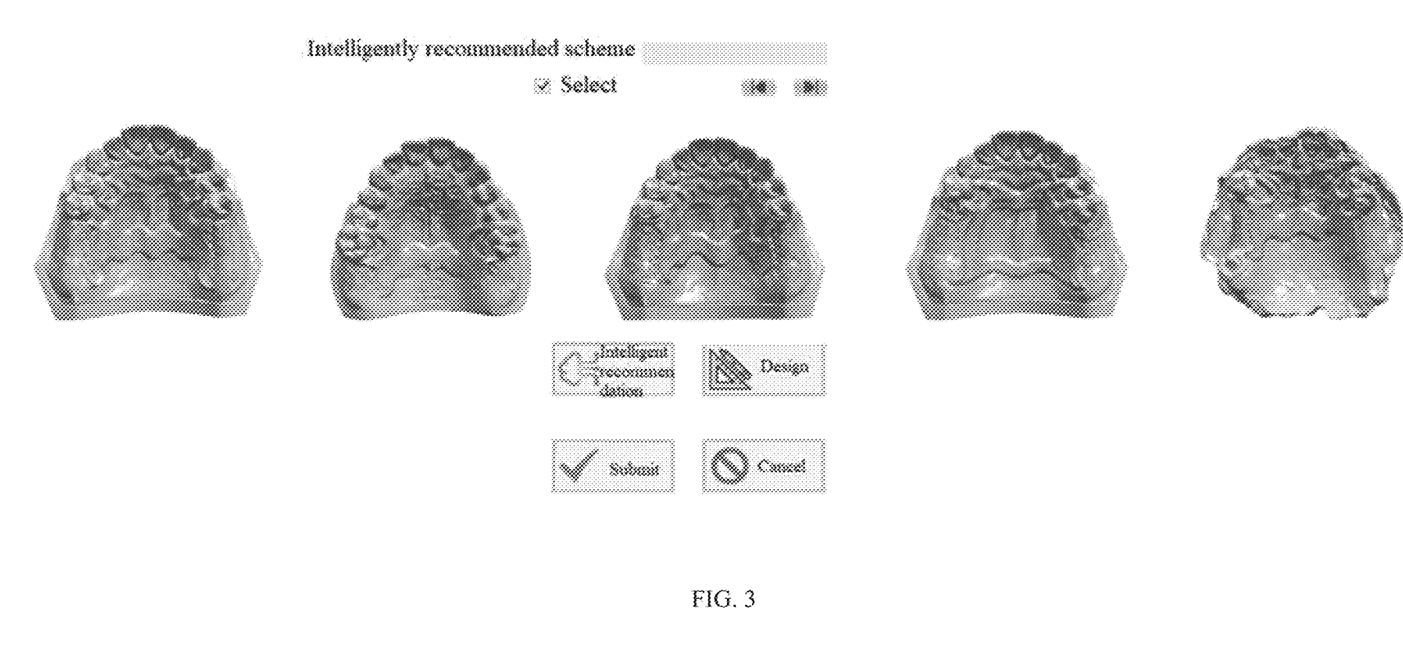
FIG. 3 shows a big data-based intelligent system for an intraoral prosthesis design scheme provided in the present disclosure, where all design schemes in the system are stored and displayed in a form of three-dimensional data.

Embodiment 2. A big data-based intelligent system for an intraoral prosthesis design scheme provided in the present disclosure, as shown in FIG. 3, includes the following modules:

(1) a module for acquiring data of intraoral partially edentulous jaw: the module implements manual, semi-manual, or automatic acquisition of data of partially edentulous jaw, and encodes data of partially edentulous jaw of a current dentition to obtain accurate code of partially edentulous jaw information, dentition accurate location code, and other dentition information code; and performs data block division on the accurate code of partially edentulous jaw information to obtain fuzzy code of partially edentulous jaw information, and calculates a data block center location of the fuzzy code of partially edentulous jaw information to obtain dentition fuzzy location code;

(2) an intraoral prosthesis design scheme database module: the module stores a large quantity of different intraoral prosthesis design schemes based on the dentition accurate location code and the dentition fuzzy location code;

(3) an intraoral prosthesis design scheme intelligent recommendation module: the module intelligently recommends an intraoral prosthesis design scheme based on the dentition accurate location code and the dentition fuzzy location code;

(4) an intraoral prosthesis design scheme intelligent modification module: the module provides an intelligent assistance tool to quickly modify the intraoral prosthesis design scheme; and (5) an intraoral prosthesis design scheme saving-to-database module: the module establishes a new intraoral prosthesis design scheme based on the dentition accurate location code and the dentition fuzzy location code.

As shown in FIG. 3, all the foregoing design schemes are stored and displayed in a form of three-dimensional data, and files of the design themes are directly used in a manufacturing device, such as a CNC cutting device or a 3D printing device.

The foregoing specific implementations and embodiments are specific support for the technical idea of the big data-based intelligent algorithm for the intraoral prosthesis design scheme provided in the present disclosure, and not intended to limit the protection scope of the present disclosure. Any equivalent change or equivalent modification made based on the technical solutions according to the technical idea of the present disclosure still fall within the protection scope of the technical solutions of the present disclosure.

What is claimed is:

1. A data-based intelligent method for selecting an intraoral prosthesis design scheme, comprising the following steps:

step S1: establishing an intraoral prosthesis design scheme database based on predetermined data of partially edentulous jaw, wherein the database provides two data search paths comprising a first search for data of partially edentulous jaw and a second search for data of partially edentulous jaw;

step S2: acquiring data of partially edentulous jaw of a dentition by using a scanning device, and performing encoding on the data of partially edentulous jaw of the dentition to obtain one group of dentition information first code, wherein the dentition information first code comprises: first code of partially edentulous jaw information, dentition first location code, and other dentition information code;

performing data block division on the first code of partially edentulous jaw information to obtain second code of partially edentulous jaw information; and calculating a data block center location of the second code of partially edentulous jaw information to obtain dentition second location code;

wherein one group of the first code of partially edentulous jaw information corresponds to one group of the second code of partially edentulous jaw information, and one group of the second code of partially edentulous jaw information corresponds to a plurality of groups of the first code of partially edentulous jaw information;

step S3: comprising a plurality of groups of intraoral prosthesis component information in the intraoral prosthesis design scheme database, wherein the intraoral prosthesis component information comprises: an intraoral prosthesis component type sequence and intraoral prosthesis component location code;

wherein the intraoral prosthesis component type sequence is a sequence formed for an intraoral prosthesis component type according to the dentition first location code in the step S2; and the intraoral prosthesis component location code comprises: intraoral prosthesis component first location code and intraoral prosthesis component second location code, wherein the intraoral prosthesis component first location code is consistent with the dentition first location code, and the intraoral prosthesis component second location code is consistent with the dentition second location code;

step S4: obtaining intraoral prosthesis design theme code according to the first code of partially edentulous jaw information in the step S2 and the intraoral prosthesis component information in the step S3, wherein the intraoral prosthesis design theme code comprises: intraoral prosthesis design first theme code and intraoral prosthesis design second theme code;

wherein the intraoral prosthesis design first theme code is a combination of a plurality of groups of first matched intraoral prosthesis component information, and the first matched intraoral prosthesis component information provides complete consistency in both the intraoral prosthesis component type sequence and the intraoral prosthesis component location code; and the intraoral prosthesis design second theme code is a combination of a plurality of groups of second matched intraoral prosthesis component information, and the second matched intraoral prosthesis component information provides complete consistency in the intraoral prosthesis component type sequence but inconsistency in the intraoral prosthesis component location code;

step S5: providing two different recommendation lists of intraoral prosthesis design schemes according to different intraoral prosthesis design concepts, specifically as follows:

step S5-1: in all intraoral prosthesis design first theme code obtained in the step S4, obtaining m pieces of intraoral prosthesis design first theme code based on one piece of first code of partially edentulous jaw information, and obtaining a first recommendation list comprising the m pieces of intraoral prosthesis design first theme code; and step S5-2: calculating to obtain n pieces of first code of partially edentulous jaw information with smallest distance function values in all intraoral prosthesis design second theme code obtained in the step S4, wherein m pieces of intraoral prosthesis design first theme code are obtained based on one piece of first code of partially edentulous jaw information, one piece of intraoral prosthesis design first theme code corresponds to one piece of intraoral prosthesis design second theme code, and obtaining a second recommendation list comprising k pieces of intraoral prosthesis design second theme code; wherein k≤n×m;

a default format of the first code of partially edentulous jaw information comprises 1 letter and 16 digits, and each of the 16 digits is either 0 or 1; the data block division dividing all adjacent and successive identical code into one data block based on one piece of first code of partially edentulous jaw information; wherein all adjacent and successive "0"s are divided into one "0" data block, and after each alternative abutment tooth is excluded, all adjacent and successive "1"s are divided into one "1" data block; in the first code of partially edentulous jaw information, if code of one tooth is 1, and code of a tooth on either side or both sides of the tooth is 0, the tooth is an alternative abutment tooth;

the calculating of the data block center location performs separate calculations of a center location of each "0" data block and a center location of each "1" data block, wherein an average value is calculated for first location code inside a dentition region corresponding to each "0" data block or each "1" data block; and step S6: displaying a plurality of intraoral prosthesis design schemes of different design themes in a three-dimensional manner, and producing a selected intraoral prosthesis design scheme from the plurality of intraoral prosthesis design schemes.

2. The data-based intelligent method for selecting the intraoral prosthesis design scheme according to claim 1, wherein the first code of partially edentulous jaw information is encoded data obtained by numbering all teeth in the current dentition according to a encoding rule after an initial posture of the dentition is adjusted, wherein the default format of the first code of partially edentulous jaw information comprises 1 letter and 16 digits, and the encoding rule is as follows:
(1) the letter: if the dentition represented by the encoded data belongs to an upper jaw, the letter is U, or if the dentition represented by the encoded data belongs to a lower jaw, the letter is L; and
(2) the digits: after the initial posture of the dentition is adjusted, teeth information in the dentition is sequentially encoded clockwise from left to right, and if a tooth is present, code of the tooth is 1, or if a tooth is absent, code of the tooth is 0;

the second code of partially edentulous jaw information is obtained by performing data block division on the first code of partially edentulous jaw information, wherein a format of the second code of partially edentulous jaw information comprises 1 letter, several "0" data blocks, several "1" digits, and several "1" data blocks, wherein a data block division rule is specifically as follows:
(3) division of the "0" data blocks: all adjacent and successive "0"s are divided into one "0" data block based on one piece of first code of partially edentulous jaw information, and the data block is marked as i–0, wherein i represents a number of data "0"s in the data block, namely a length of the "0" data block;
(4) division of the "1" digits: each alternative abutment tooth is used as a separate "1" digit based on the one piece of first code of partially edentulous jaw information; and
(5) division of the "1" data blocks: after each alternative abutment tooth is excluded, all adjacent and successive "1"s are divided into one "1" data block based on the one piece of first code of partially edentulous jaw information, and the data block is marked as j–1, wherein j represents a number of data "1"s in the data block, namely a length of the "1" data block.

3. The data-based intelligent method for selecting the intraoral prosthesis design scheme according to claim 1, wherein the dentition first location code is obtained by encoding a dentition location based on the first code of partially edentulous jaw information after an initial posture of the dentition is adjusted, and a specific rule is as follows: first location code is sequentially 1, 2, 3, 4, 5, 6, 7, 8, 9, 10, 11, 12, 13, 14, 15, and 16 in a clockwise direction from left to right; and the dentition second location code is obtained by calculating the data block center location of the second code of partially edentulous jaw information, and a calculation rule of the data block center location is: the center location is calculated for each "0" data block or each "1" data block in the second code of partially edentulous jaw information, and the average value is calculated for the accurate location first location code inside the dentition region corresponding to each "0" data block or each "1" data block.

4. The data-based intelligent method for selecting the intraoral prosthesis design scheme according to claim 1, wherein the other dentition information code is other teeth information obtained based on the one piece of first code of partially edentulous jaw information, comprising:
(1) a tooth loosening degree coefficient: for a tooth with code of 1, if code of a tooth on either side or both sides of the tooth is 0, the tooth is defined as an alternative abutment tooth, and a loosening degree coefficient of the tooth is obtained; for a tooth with code of 1, if code of teeth on both sides of the tooth is 1, the tooth is defined as a general abutment tooth, and a loosening degree coefficient of the tooth is obtained; and the loosening degree coefficient is any decimal between 0 and 1, and a smaller number represents a more severe tooth loosening degree; and
(2) a tooth rotation matrix: for a tooth with code of 1, a three-dimensional rotation matrix $M_t$ is defined to reflect a relationship between an actual space state and a standard healthy state of the tooth, wherein the subscript t is the dentition first location code.

5. The data-based intelligent method for selecting the intraoral prosthesis design scheme according to claim 1, wherein the intraoral prosthesis component type comprises: a first intraoral prosthesis component type, a second intraoral prosthesis component type, and a third intraoral prosthesis component type;

wherein the first intraoral prosthesis component type is a component related to the dentition first location code;

the second intraoral prosthesis component type is a secondary component weakly related to the dentition first location code; and the third intraoral prosthesis component type is a component that connects the first intraoral prosthesis component type to the second intraoral prosthesis component type.

6. The data-based intelligent method for selecting the intraoral prosthesis design scheme according to claim 1, further comprising a sorting method of the intraoral prosthesis design second theme code in the second recommendation list as follows:

(1) sorting based on partially edentulous jaw information of a patient;
performing sorting according to an ascending order of distance function values of the first code of partially edentulous jaw information; to be specific, a smaller distance function value indicates a higher sorting location of the intraoral prosthesis design second theme code corresponding to the first code of partially edentulous jaw information; wherein for any two pieces of different first code of partially edentulous jaw information, a case in which the two pieces of different first code of partially edentulous jaw information correspond to identical second code of partially edentulous jaw information exists; in this case, a calculation method of a distance function between the two pieces of different first code of partially edentulous jaw information is as follows:

$$D = \sum_{1}^{i} |(a_i - b_i)|$$

wherein the dentition second location code of first code of partially edentulous jaw information is $a_1 a_2 \ldots a_i$, and the dentition second location code of second first code of partially edentulous jaw information is $b_1 b_2 \ldots b_i$, $1 \leq i \leq 16$;

sorting is performed according to the other dentition information code, and the other dentition information code comprises a tooth loosening degree coefficient and a tooth rotation matrix; and (2) custom sorting based on subjective and objective scoring results;

experts subjectively score design themes from dimensions of hygiene, mechanical balance, and aesthetics; at the same time, finite element calculation and in vitro mechanical verification are introduced to objectively score the design themes to obtain subjective and objective scoring results, and the subjective and objective scoring results provide a basis for user-defined theme sorting.

7. The data-based intelligent method for selecting the intraoral prosthesis design scheme according to claim 1, further comprising a process of supplementing the intraoral prosthesis design scheme database with new partially edentulous jaw information code as follows:

when no design theme corresponding to new data of partially edentulous jaw is found in the database by either the first search for the data of partially edentulous jaw or the second search for the data of partially edentulous jaw, a dental technician or a doctor first complete a concept of a required intraoral prosthesis design scheme and submit the intraoral prosthesis design scheme, and various new first code and second code of the data of partially edentulous jaw are automatically created.

\* \* \* \* \*